United States Patent [19]
Kratsch et al.

[11] Patent Number: 5,478,350
[45] Date of Patent: Dec. 26, 1995

[54] RACK AND PINION ACTUATOR HANDLE FOR ENDOSCOPIC INSTRUMENTS

[75] Inventors: Peter K. Kratsch, Sunrise; Kevin F. Hahnen, Ft. Lauderdale, both of Fla.

[73] Assignee: Symbiosis Corporation, Miami, Fla.

[21] Appl. No.: 275,291

[22] Filed: Jul. 14, 1994

[51] Int. Cl.⁶ .................................................. A61B 17/28
[52] U.S. Cl. .......................... 606/205; 606/174; 128/751
[58] Field of Search ...................... 606/51, 52, 205–210, 606/174; 128/750–755

[56] References Cited

U.S. PATENT DOCUMENTS 4,467,802  8/1984  Maslanka ................... 606/206
5,275,615  1/1994  Rose .
5,282,806  2/1994  Haber et al. .

FOREIGN PATENT DOCUMENTS 9320759  10/1993  WIPO ..................... 606/205

*Primary Examiner*—Stephen C. Pellegrino
*Assistant Examiner*—William W. Lewis
*Attorney, Agent, or Firm*—David P. Gordon

[57] ABSTRACT

An actuator mechanism for an endoscopic instrument includes a stationary handle having a stepped throughbore with a relatively smaller diameter at the distal end and a relatively larger diameter at the proximal end. A cylindrical rack member is slidably disposed in the larger diameter portion of the throughbore. The larger diameter portion of the throughbore has a lower slot opening, and a movable lever is pivotally coupled to the stationary handle and is provided with a toothed upper pinion which enters the slot in the larger diameter portion of the throughbore and engages the rack member. The proximal end of the tube member is coupled to the distal smaller diameter portion of the throughbore and the proximal end of the control member is coupled to the distal end of the rack member.

18 Claims, 8 Drawing Sheets

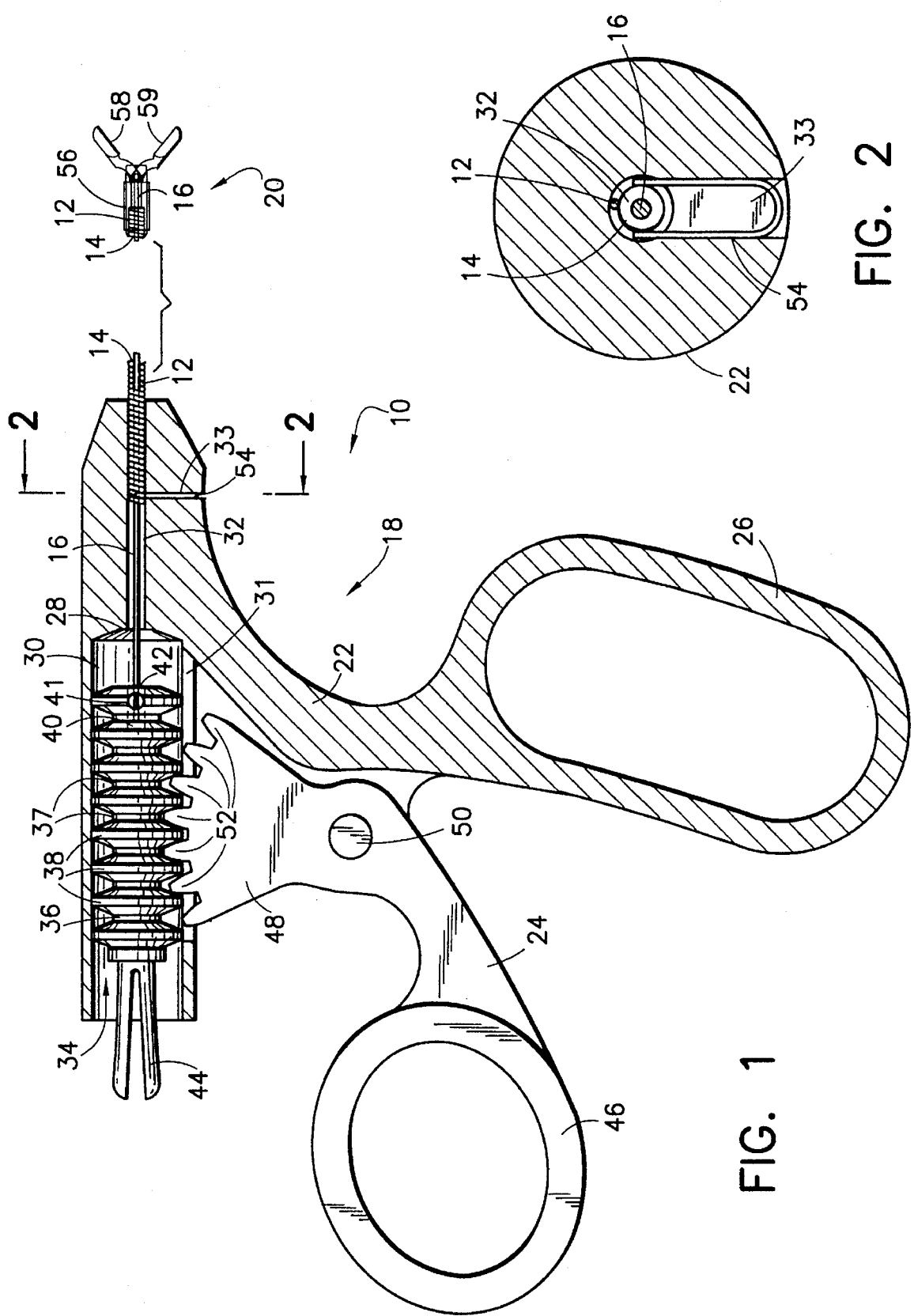

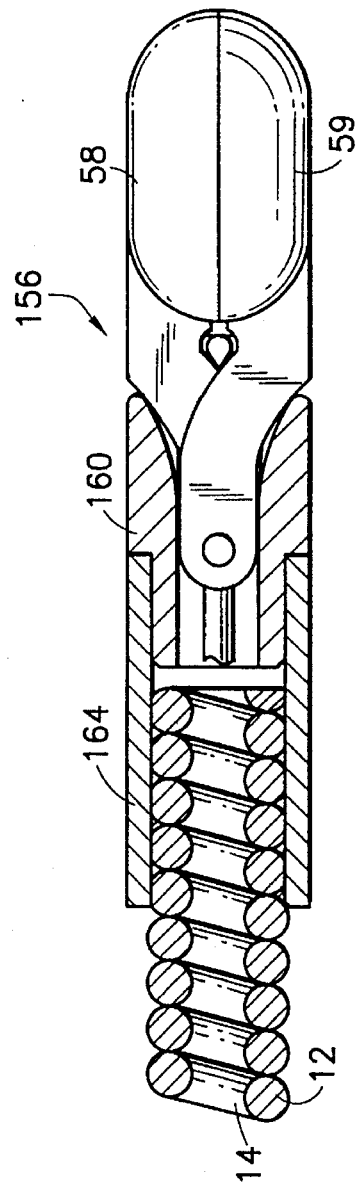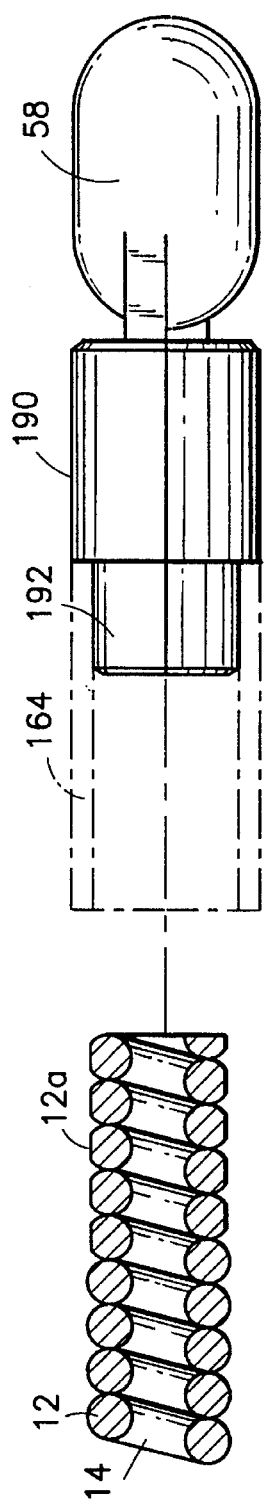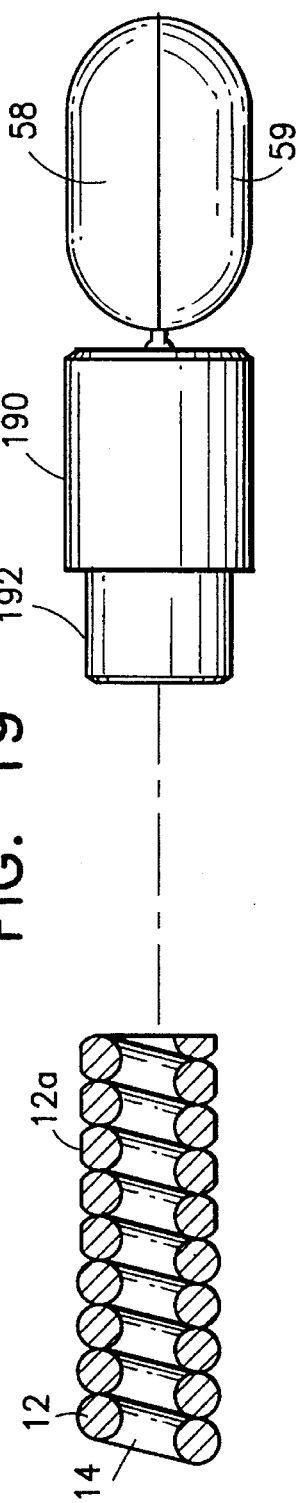

RACK AND PINION ACTUATOR HANDLE FOR ENDOSCOPIC INSTRUMENTS

BACKGROUND OF THE INVENTION

1. Field of the Invention

This invention relates to endoscopic surgical instruments. More particularly, this invention relates to an endoscopic forceps having a rack and pinion actuator handle and a track guided end effector assembly.

2. State of the Art

Endoscopic forceps are well known in the art. These instruments typically include a tube member and a control member extending through the tube member. The proximal end of the control member is typically coupled to an actuator handle which imparts reciprocal movement to the control member relative to the tube member. The distal end of the tube member is typically coupled to a clevis and a pair of forceps end effectors are pivotally mounted in the clevis. The distal end of the control member is coupled to the end effectors and reciprocal movement of the control member relative to the tube member causes the end effectors to pivot relative to the clevis and thereby open or close relative to each other. The tube member and the control member may be either rigid or flexible and the length of these members will vary, depending on the application, from several inches to several feet.

Several different kinds of actuator mechanisms are known for use with endoscopic forceps, including a handle-lever gripping member arrangement, and a thumb ring-spool type device. The handle-lever arrangement includes a stationary handle and a movable lever which is pivotally coupled to the stationary handle. The stationary handle has a distal finger ring and the movable lever has a proximal thumb ring. The stationary handle is coupled to the tube member and the movable lever is coupled to the control member. Typically, the handle-lever mechanism is held like a pair of scissors. Squeezing the thumb ring towards the finger ring pulls the control member in a proximal direction which usually results in closing the end effectors. The thumb ring-spool devices usually include a central slotted shaft having a proximal thumb ring, where the displaceable spool is slidable along the shaft and has a cross member which passes through the slot in the shaft. The tube member is coupled to the shaft and the control member is coupled to the cross member of the spool. The thumb ring-spool device is held like a hypodermic syringe. Squeezing the spool towards the thumb ring usually results in closing the end effectors.

Various designs for the clevis and end effectors are also known, although the clevis is most often a U-shaped member having an axle pin on which a pair of end effectors is pivotally mounted. The end effectors may be cutters or grippers. In the case of biopsy forceps, the end effectors are typically formed to be cuplike for holding a tissue sample which is cut or torn by the forceps.

There are many concerns in the design and manufacture of endoscopic forceps and these concerns are often related to the competing interests of strength versus cost of manufacture. The materials used in most endoscopic instruments include stainless steel and aluminum. More recently, in disposable instruments, plastic and bronze have been used. Manufacturing processes include molding, casting and extrusion. Typically, the end effectors are the most difficult part of the endoscopic instrument to manufacture because of their small size and because they must be strong. In cutting and biopsy instruments, the coupling of the end effectors to the clevis, the clevis to the tube member, and the end effectors to the control member raise additional strength considerations since the amount of force required to cut and/or obtain a biopsy tissue sample is relatively high. In addition, clogging of the clevis and the tube is always a consideration since various fluids and tissues may enter the clevis space and hamper operation of the forceps.

While the handle actuator is usually easy to manufacture, due in part to its relatively large size compared to the end effectors and the clevis, there are several considerations which must be addressed regarding the actuator handle. Among these considerations are smooth action, tactile feedback, and linear motion. These considerations are also often related to the clevis and end effector assembly insofar as the end effectors should move positively and smoothly in response to the movement of the actuator handle and the actuator handle should provide tactile feedback in response to the action of the end effectors. The amount of movement of the handle actuator needed to open and close the end effectors is also an important consideration.

SUMMARY OF THE INVENTION

It is therefore an object of the invention to provide an endoscopic forceps which has enhanced strength but is inexpensive to manufacture.

It is also an object of the invention to provide an endoscopic forceps having an actuator handle which imparts true linear motion to the control member.

It is another object of the invention to provide an endoscopic forceps having an actuator handle which transmits positive tactile feedback to the user.

It is a further object of the invention to provide an endoscopic forceps having an actuator handle which allows rotation of the forceps.

Another object of the invention is to provide an end effector assembly which has enhanced strength but is inexpensive to manufacture.

A further object of the invention is to provide end effectors which have enhanced strength but art inexpensive to manufacture.

Even another object of the invention is to provide a clevislike coupling device which has enhanced strength but is inexpensive to manufacture.

It is still another object of the invention to provide a clevis which resists clogging by tissues and fluids.

It is also an object of the invention to provide a clevis and end effectors in which the rate at which the end effectors open and close relative to a given movement of the actuator can be preselected.

Yet another object of the invention to provide a clevis and end effectors in which the closing force of the end effectors can be enhanced for cutting end effectors or reduced for grasping end effectors.

In accord with these objects which will be discussed in detail below, the endoscopic forceps of the present invention includes a tube member and a control member extending through the tube member. The proximal ends of the control member and the tube member are coupled to an actuator mechanism which imparts reciprocal movement to the control member relative to the tube member. The actuator mechanism according to the invention includes a handle part having a stepped throughbore with a relatively small diameter at the distal end and relatively large diameter at the proximal end. The large diameter portion of the throughbore has a lower slot opening and a cylindrical rack member is slidably disposed in the large diameter portion of the throughbore. A lever is pivotally coupled to the stationary handle and is provided with a toothed upper pinion which enters the slot in the large diameter portion of the throughbore and engages the rack member. The proximal end of the tube member is coupled to the distal small diameter portion of the throughbore and the proximal end of the control member is coupled to the distal end of the rack member.

According to a preferred aspect of the invention, the rack member is provided with a distal bore and a radial set screw which enters the distal bore. The control member is preferably a push rod or wire which is coupled to the rack member by inserting the proximal end of the push rod into the distal bore of the rack member and tightening the set screw. In a rotational embodiment, a rotational ferrule is coupled to the tube member and can be rotated relative to the handle. When the ferrule is rotated, the tube member, end effectors, push rod or wire, and rack member all rotate, with the cylindrical rack member rotating in the toothed pinion. In a non-rotational embodiment, the distal small diameter portion of the throughbore in the handle is preferably provided with a radial slot which extends to the exterior of the handle. The tube member is preferably a coil which is coupled to the handle by inserting the proximal end of the coil into the small diameter portion of the throughbore in the handle and inserting a staple into the radial slot such that the staple engages turns of the coil or a slot in the tube but permits free movement of the push rod or wire.

The distal end of the tube member is coupled to a clevis and a pair of end effectors are engaged by the clevis and coupled to the distal end of the control member. For purposes herein, the term "clevis" is to be understood broadly as the structural apparatus which holds or guides the end effectors, regardless of its shape and structure, and is not to be defined in a limited manner to be limited to U-shaped devices. The clevis according to the invention is a cylindrical plastic or metal member formed from two substantially identical halves. Each half of the clevis has a proximal semi-cylindrical opening, and a distally extending longitudinal groove which bends outward from the longitudinal axis at the distal end of the clevis half and forms a track for guiding movement of a respective end effector. A portion of the clevis half has a sleeve-receiving waist of slightly reduced outer diameter. According to one embodiment, the clevis is provided with a deformation-permitting side cut-out, and a tube engaging bump located on an inner surface of the proximal semi- cylindrical opening between the side cut-out and the distally extending longitudinal groove. The two halves of the clevis are assembled by joining the halves over the distal end of the tube member and sliding a substantially rigid sleeve over the waists of the halves. The sleeve is able to assume its position over the waists due to the deformation-permitting side cut-outs which radially yield as the sleeve is forced over collars on the clevis halves. When assembled in this manner, the tube engaging bump deforms into the tube member, thereby holding the tube member in place in the clevis. According to another embodiment, the clevis is provided with a reduced diameter proximal portion over which a sleeve which connects the coil to the clevis can be crimped or otherwise attached. Regardless of the mechanism for attaching the clevis to the tube or coil, the distal end of the assembled clevis presents a substantially flat circular surface except for distal ends of the two oppositely directed outwardly bending longitudinal grooves; each of which present a small, substantially rectangular opening on the distal base of the clevis and a small, substantially rectangular radial opening adjacent to and contiguous with the base opening.

The end effectors according to the invention are preferably identical and each has a proximal tang which is offset from the longitudinal axis of the end effector and which curves through the plane of the working surface of the end effector. The tang of each end effector is received by a respective longitudinal groove of the clevis and the end of each tang is coupled to the distal end of the control member. When the control member is moved distally through the tube member, the tangs of the end effectors are guided in their distal movement by the inner surfaces of the grooves in the clevis and the working surfaces of the end effectors are moved apart from each other. When the control member is moved proximally through the tube member, the tangs of the end effectors are guided in their proximal movement by the grooves in the clevis and the working surfaces of the end effectors are moved towards each other. The curvature and/or the angle of the bends in the tangs and/or the clevis grooves determine how fast the end effectors open and close relative to a given movement of the control member. Since the only opening of the clevis is through the grooves and since these grooves are occupied by the end effector tangs, the clevis is substantially sealed from clogging by fluids or tissues.

According to preferred aspects of the invention, the distal end of the push rod is provided with a hooked bend and the tangs of the end effectors are provided with holes which are engaged by the hooked end of the push rod. The clevis is preferably provided with slots along a portion of the longitudinal grooves for receiving the sides of the hooked end of the push rod. The clevis is preferably molded 30% carbon fiber filled nylon and the groove arrangement provides smooth operation and high strength.

Attachment of the clevis and end effectors to the distal ends of the coil and push rod is preferably accomplished by first inserting the push rod-through the tube or coil and placing the clevis sleeve over the distal end of the tube or coil. The tangs of the end effectors are then coupled to the end of the push rod, and the halves of the clevis are placed around the end effectors so that the tangs of the end effectors engage the grooves in the clevis. Where the clevis includes tube engaging bumps, the placement of the clevis will cause the bumps to engage the tube or coil. The sleeve is then slid over the clevis halves.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation view in partial section of a rack and pinion actuator handle according to the invention coupled to a coil and push rod and a track guided end effector assembly according to the invention;

FIG. 2 is an enlarged cross sectional view along line 2—2 of FIG. 1;

FIG. 18 is an enlarged side elevation view in partial section of a second embodiment of the clevis of the invention coupled to the distal end of a coil;

FIG. 19 is an enlarged exploded top view in partial section of the clevis of FIG. 18; and FIG. 20 is an enlarged exploded side elevation view in partial section of the clevis of FIG. 18.

DETAILED DESCRIPTION OF THE PREFERRED EMBODIMENTS

Figure 1A:
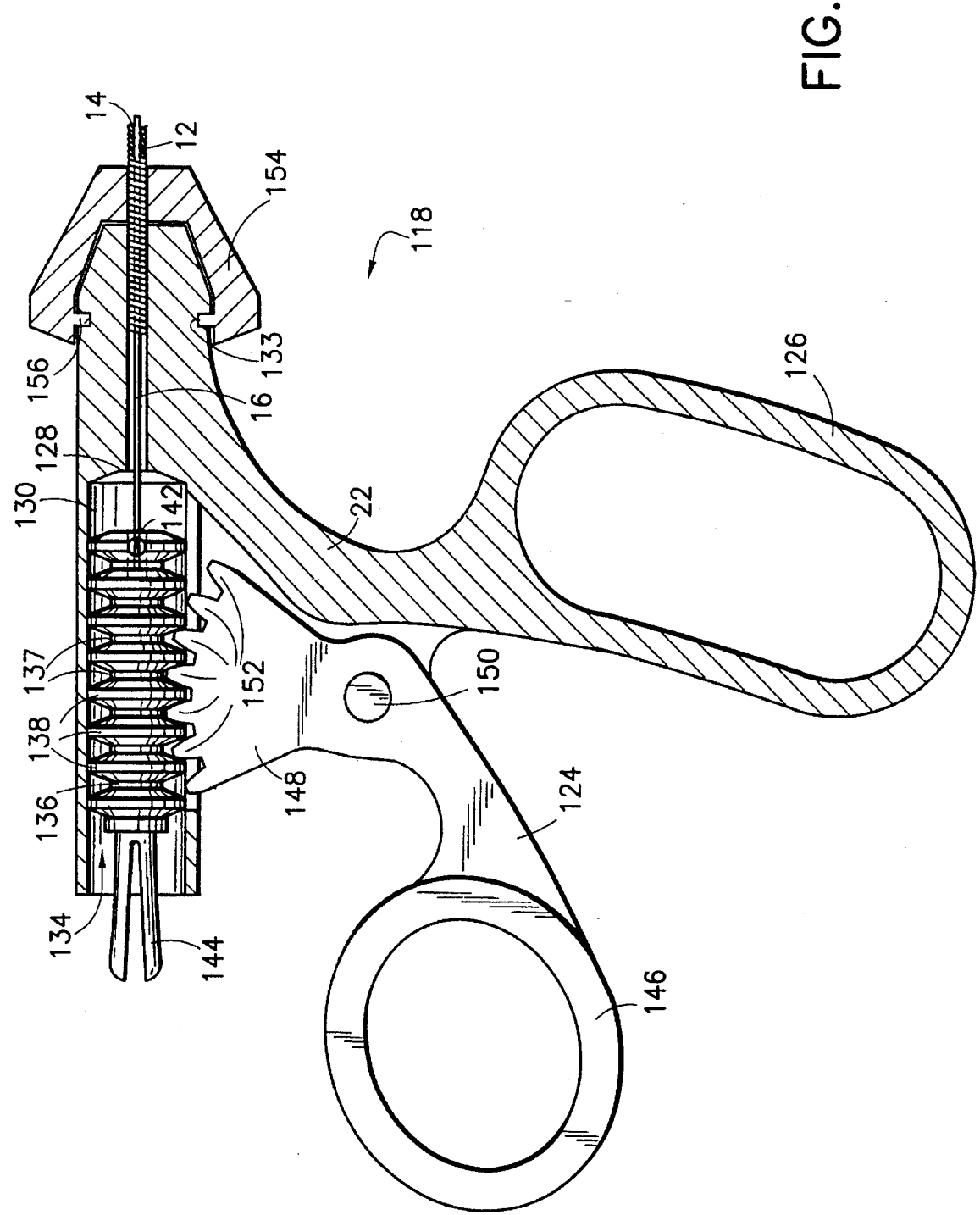
FIG. 1a is a view similar to FIG. 1 of a second embodiment of an actuator handle according to the invention.

Referring now to FIGS. 1 and 2, an endoscopic forceps 10 according to the invention includes a flexible coil 12 having a lumen 14 and a push rod or wire 16 extending through the lumen 14 of the coil 12. A proximal actuator mechanism 18 is coupled to the proximal ends of the coil 12 and the push rod 16 for imparting reciprocal movement to the push rod relative to the coil. A distal end effector assembly 20 is coupled to the distal ends of the coil 12 and the push rod 16 and is responsive to reciprocal movement to the push rod relative to the coil.

The actuator mechanism 18, according to the invention, includes a stationary handle 22 and a movable lever 24. The stationary handle 22 has a lower finger ring 26 and an upper stepped through bore 28. The stepped throughbore 28 has a larger diameter proximal portion 30 and a smaller diameter distal portion 32. The larger diameter portion 30 is provided with a lower slot opening 31 and the smaller diameter portion 32 is provided with a radial slot 33 which extends to the exterior of the stationary handle 22. A cylindrical rack member 34 is slidably disposed in the larger diameter portion 30. The rack member 34 has a cylindrical shaft 36 and a plurality of cogs 38 spaced apart by defining grooves 37. The distal end of the rack member 34 is provided with a longitudinal bore 40 for receiving the rod or wire(s) 16, and a radial bore for accommodating a radial set screw 42 which enters the longitudinal bore 40 for holding the rod or wire(s) therein. The proximal end of the rack member 34 is preferably provided with an electrical connector such as a banana clip 44 for connection to a source of cautery current (not shown).

The movable lever 24 of the actuator mechanism 18 has a lower thumb ring 46 and an upper pinion 48. The movable lever 24 is coupled to the stationary handle 22 by a pivot axle 50 and is arranged so that the upper pinion 48 enters the larger diameter portion 34 of the throughbore 28 through the lower slot opening 31. The upper pinion 48 is curved with a radius "r" extending from the pivot axle 50 to the closest groove 37 and has a plurality of spaced apart teeth 52. The teeth 52 engage the spaces (grooves) 37 between the cogs 38 on the rack member 34 as seen in FIG. 1. From the foregoing, those skilled in the art will appreciate when the movable lever 24 is rotated about the pivot axle 50, the pinion 48 imparts a true linear reciprocal motion to the rack member 34.

The actuator mechanism 18 is coupled to the tube or coil 12 and push rod or wire(s) 16 by first inserting the proximal end of the push rod or wire(s) 16 into the bore 40 of the rack member 34 and tightening the set screw 42. The proximal end of the tube or coil 12 is then inserted into the smaller diameter portion 32 of the throughbore 28 past the radial slot 33. A staple 54 (or any substantially U-shaped member) is inserted into the slot 33 until it engages the coil or tube 14, with the legs of the staple embedding into the handle. According to one embodiment of the invention, where a coil is utilized, the legs of the staple extend between turns of the coil (as seen in FIG. 2) and prevent the coil from being pulled out of the handle. According to another embodiment of the invention, the cross piece of the staple is located such that it extends between turns of the coil to prevent the coil from being pulled out of the handle. If desired, the legs may be similarly arranged. Regardless, care must be taken to avoid impeding movement of the push rod or wire 16 through the coil 12. According to yet another embodiment of the invention, instead of providing a radial slot 33, two holes are provided for the legs of the staple, which are placed to between turns of the coil so as to prevent the coil from being pulled out of the handle. When the staple legs are embedded into the handle, the staple cross piece can be flattened or rounded against the external surface of the handle.

FIG. 1a shows a second embodiment of the actuator mechanism 118 which is similar in many respects to the actuator mechanism 18 of FIG. 1. In FIG. 1a, similar features of the actuator mechanism 118 have reference numerals which are similar to those used with reference to the actuator mechanism 18, but increased by one hundred. In the second embodiment seen in FIG. 1a, the actuator mechanism 118 is provided with radial groove 133 in lieu of a staple slot 33. A rotational ferrule 154 is also provided and is bonded or otherwise attached to the coil or tube 12. Alternatively, a proximal portion of the coil or tube 12 is insert molded in the ferrule 154. The ferrule 154 is provided with a groove engaging radially inward projection 156 which engages and rides in the radial groove 133. The ferrule is preferably made from resilient plastic and is press fit over the actuator 118 so that the projection 156 snaps into the groove 133. The ferrule 154 is thus rotatable relative to the actuator 118. As will be appreciated by those skilled in the art, rotation of the ferrule 154 relative to the actuator mechanism 118 will effect a rotation of the coil 12 and thereby effect rotation of the end effector assembly 20 (FIG. 1). Rotation of the end effector assembly will result in a rotation of the push rod or wires 16. The rotation of the push rod or wires 16 will result in a rotation of the rack member 134 inside the large diameter proximal portion 130 of the throughbore 128 with the preferably rounded cogs 138 rotating in the teeth 152 of the pinion 148. It will therefore be recognized that the rack and pinion arrangement according to the invention allows for easy rotation of the coil and push rod relative to the actuator mechanism. The ferrule shown in FIG. 1a is merely exemplary. Other ferrules which may be applied to the actuator mechanism are disclosed in co-assigned U.S. Pat. Nos. 5,176,702; 5,174,300; and 5,293,878, the disclosures of which are hereby incorporated herein by reference in their entireties. If desired, the groove 133 and the projection 156 may be provided with bumps and indents (not shown) so that rotation of the ferrule is stepped.

Figure 3:
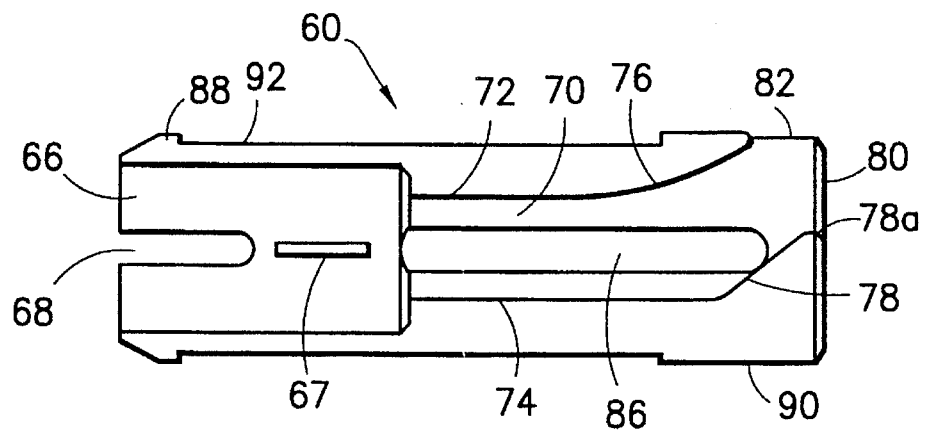
FIG. 3 is an enlarged side elevation view of a clevis half according to the invention.
Figure 4:
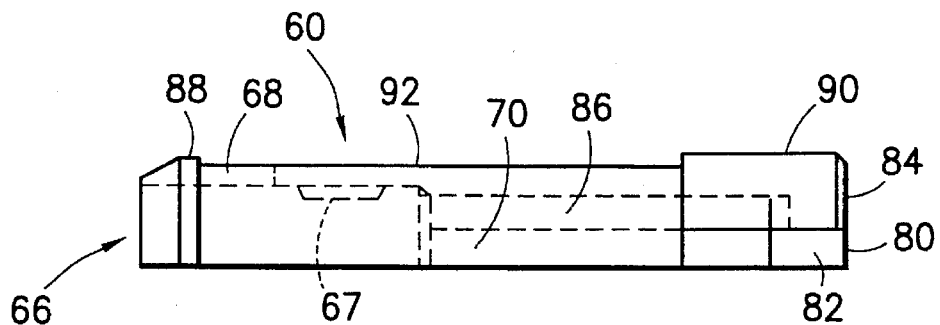
FIG. 4 is a top view of the clevis half of FIG. 3.
Figure 5:
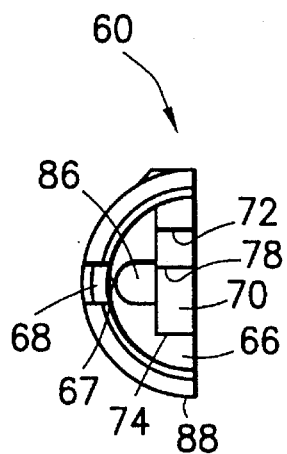
FIG. 5 is a proximal end view of the clevis half of FIG. 3.
Figure 6:
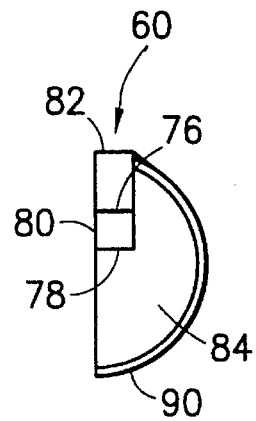
FIG. 6 is a distal end view of the clevis half of FIG. 3.
Figure 7:
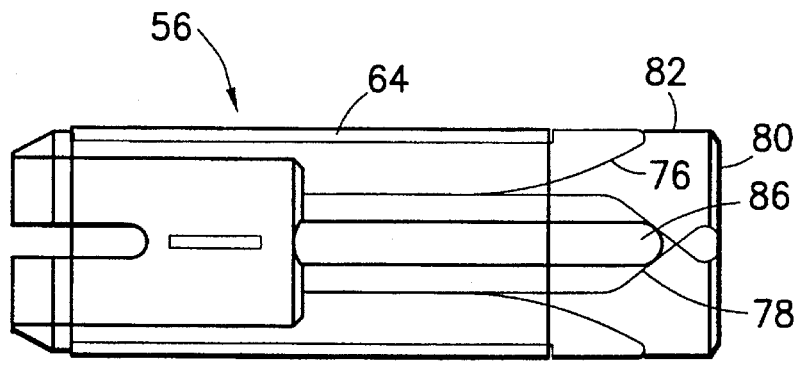
FIG. 7 is an enlarged transparent side elevation view of two clevis halves held together with a sleeve according to the invention.
Figure 8:
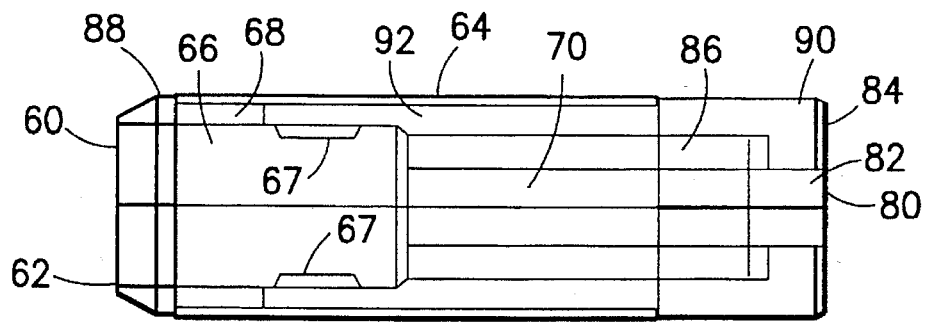
FIG. 8 is a top view of the clevis halves of FIG. 7.
Figure 9:
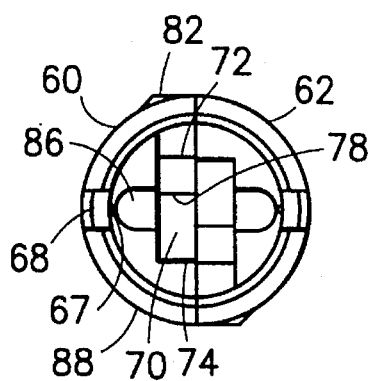
FIG. 9 is a proximal end view of the clevis halves of FIG. 7.
Figure 10:
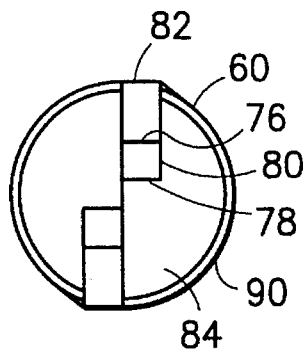
FIG. 10 is a distal end view of the clevis halves of FIG. 7.

The end effector assembly 20, according to the invention, includes a clevis 56 and a pair of preferably identical end effectors 58, 59 which are seen in detail in FIGS. 4 through 10. In one embodiment, the clevis 56 is formed from two substantially identical clevis halves 60 (62) which are joined together with a stainless steel sleeve 64 as seen best in FIGS. 8 through 10 and described in more detail below. Each clevis half, for example 60 (FIGS. 3 through 6), is a molded plastic semi-cylindrical member. (For simplicity, only clevis half 60 is described and referenced with numerals, since both clevis halves 60 and 62 are substantially identical.) A semi-cylindrical opening 66 is provided at the proximal end of the clevis half 60. A deformation-permitting side cut-out 68 is provided in the side wall of the opening 66 and a coil engaging bump 67 is provided in the side wall distal of the cut-out 68. A longitudinal groove 70 extends from the distal end of the opening 66 towards the distal end of the clevis half 60 and bends away from the longitudinal axis of the clevis half at the distal end of the clevis half. The groove 70 is defined by two sidewalls 72, 74 which are substantially parallel near the opening 66 and which bend at different rates near the distal end of the clevis half 60. As seen best in FIG. 3, the upper sidewall 72 bends smoothly in a shallow arc 76 toward the top of the clevis half and ends before the distal end of the clevis half 60. The lower sidewall 74 bends up more rapidly at 78 and ends at the distal end of the clevis half 60 with a curved downward dip 78a. The slot 70 thereby exits the clevis half 60 through two substantially rectangular openings 80, 82. Other than the opening 80, the distal end of the clevis half 60 is a solid semicircular surface as seen best in FIGS. 6 and 10. A longitudinal slot 86 is preferably provided within the groove 70 for reasons which will be described below. In the preferred embodiment, the outer surface of the clevis half 60 is a substantially smooth semi-cylinder except for a ramped proximal collar 88 and a distal collar 90 defining a central sleevereceiving waist 92. The proximal collar 88 is preferably provided with a conical taper or ramp 89 to aid in the reception of the sleeve 64 as described below. The stainless steel sleeve 64 is seated on the waist 92 between the collars (protrusions) 88 and 90 when the clevis is assembled as shown in FIGS. 7 and 8.

Figure 11:
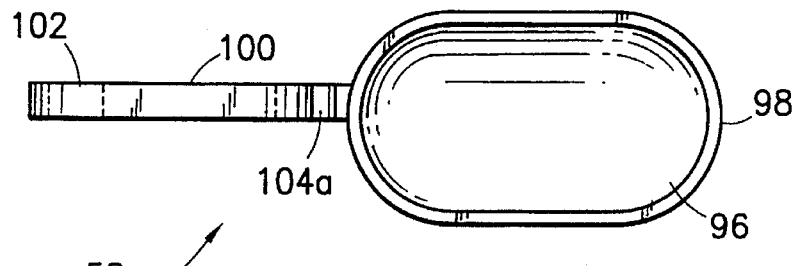
FIG. 11 is an enlarged top view of a first embodiment of an end effector according to the invention.
Figure 12:
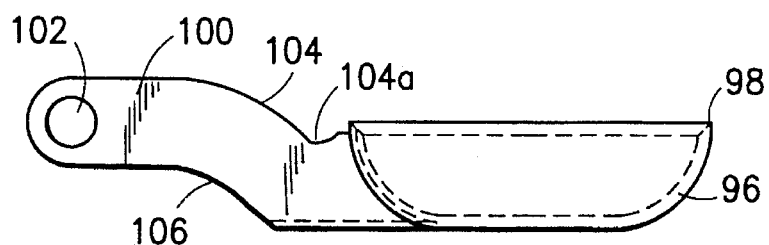
FIG. 12 is a side elevation view of the end effector of FIG. 11.
Figure 13:
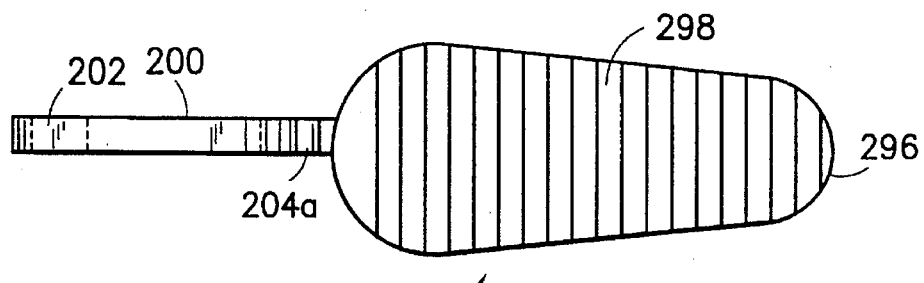
FIG. 13 is an enlarged top view of a second embodiment of an end effector according to the invention.
Figure 14:
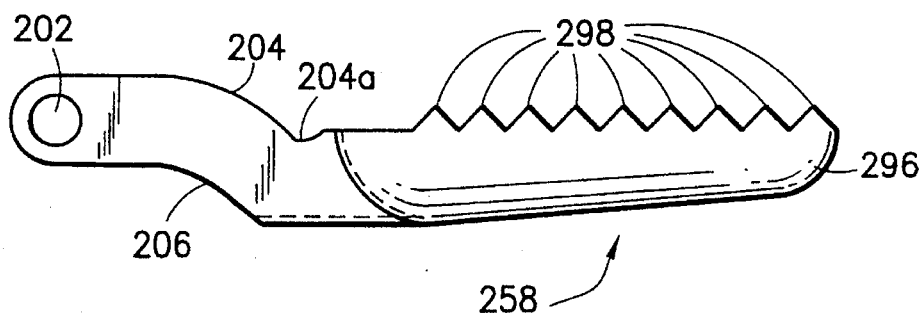
FIG. 14 is a side elevation view of the end effector of FIG. 13.

One of the pair of identical end effectors 58 designed for use with the clevis 56 is shown in FIGS. 11 and 12. (For simplicity, only end effector 58 will be described and referenced with numerals since both end effectors 58 and 59 are identical.) End effector 58 is a biopsy forceps end effector and has a substantially oblate hemispherical cup portion 96 which may be provided with a relatively sharp lip 98. A proximal tang 100 is offset from the longitudinal axis of the cup 96 and extends substantially parallel to the longitudinal axis of the cup 96. The proximal end of the tang 100 is provided with a hole 102 for coupling with the push rod as will be described in detail below. As seen best in FIG. 12, the tang 100 is shaped like a pan handle and rises above the plane in which the lip 98 lies. A relatively shallow curved surface 104 with a rounded notch 104a is provided on one edge of the tang and a slightly steeper curved surface 106 is provided on an opposite edge of the tang 100. As will be appreciated from the discussion below, the tang is a particularly important aspect of the end effector 58, while the cup 96 may be replaced with virtually any type of end effector element such as a gripper 296 as shown in FIGS. 13 and 14, a scissors (not shown), a serrated biopsy cup (not shown), etc. The end effector 258 shown in FIGS. 13 and 14 is substantially paddle shaped with a grooved working surface 298 for gripping. The tang 200, however, is virtually identical to the tang 100 described above having similarly curved edge 204 with rounded notch 204a and curved edge 206.

Figure 15:
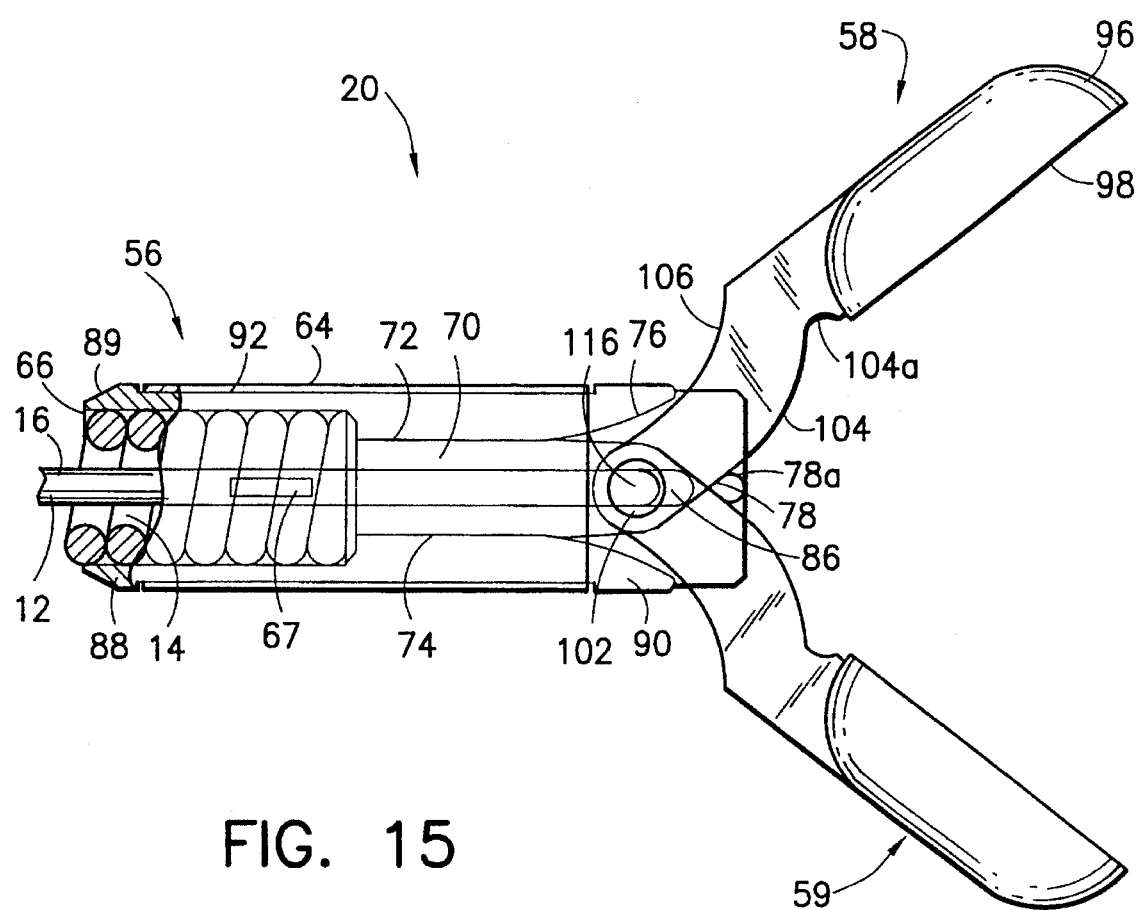
FIG. 15 is an enlarged transparent side elevation view of the clevis of the invention coupled to the distal end of a coil and two end effectors mounted in the clevis and coupled to the distal end of a push rod, with the end effectors in the open position.
Figure 16:
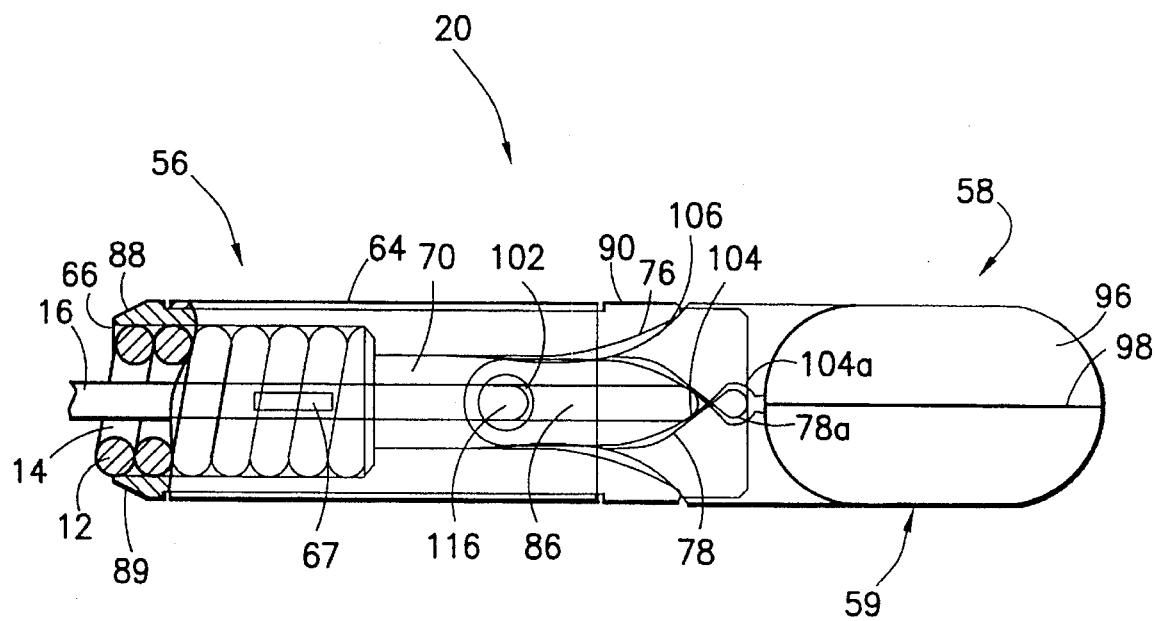
FIG. 16 is a view similar to FIG. 15, but with the end effectors in the closed position.
Figure 17:
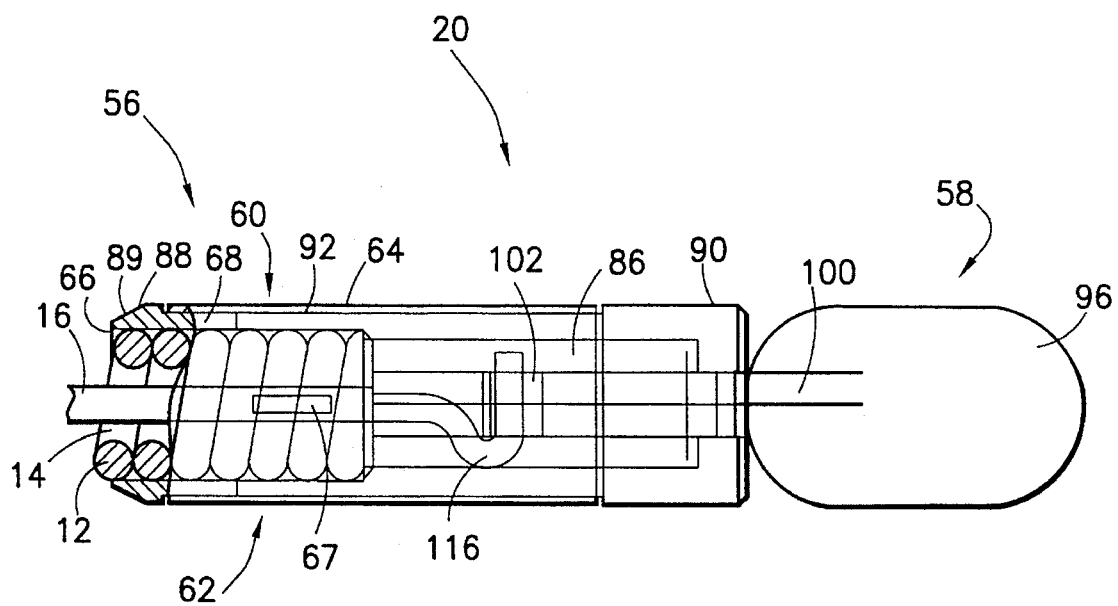
FIG. 17 is an enlarged transparent top view of the clevis of the invention coupled to the distal end of a coil and two end effectors mounted in the clevis and coupled to the distal end of a push rod, with the end effectors in the closed position.

FIG. 15 through 17 illustrate how the preferred embodiment of the clevis 56 and the end effectors 58 (59) are assembled, how they are coupled to the coil 12 and the push rod 16, and how they operate in response to the actuation handle. Turning to FIG. 17, it will be seen that the distal end of the push rod 16 is bent to form a hook 116 which engages the holes 102 in the tangs 100 of the end effectors 58 (59). It will also be seen that the longitudinal slots 86 in the clevis halves 60 (62) provide a space for the hook 116 as well as a guiding track for the push rod 16 as it is moved to the distal position shown in FIG. 15 and the proximal position shown in FIGS. 16 and 17.

As mentioned briefly above, the end effector assembly 20 is assembled by first inserting the push rod 16 into the lumen 14 of the coil 12 (before the coil and push rod are coupled to the handle as described above with reference to FIGS. 1 and 2). The clevis sleeve 64 is placed temporarily over the distal end of the coil 12 and the two end effectors 58, 59 are attached to the hook 116 at the distal end of the push rod 16 as shown best in FIGS. 16 and 17. Next, the clevis halves 60, 62 are placed over the tangs 100 of the end effectors so that respective tangs reside in respective grooves 70 and the hook 116 resides in the slots 86 and the proximal semi-cylindrical openings 66 embrace the distal end of the coil 12. In this state, the bumps 67 press against the turns of the coil 12. The sleeve 64 is then moved off the distal end of the coil 12 and over the conical tapers 89 of the proximal collars 88 of the clevis halves 60, 62. As the sleeve rides up the ramps, the proximal collars 88, due to the cut-outs 68, bend slightly radially inward, so that the sleeve can be forced over and past the collars 88. The sleeve 64 is then slid onto the waist 92 of the clevis where it is secured between the proximal and distal collars 88 and 90 (collars 88 having resumed an unstressed position) and holds the two clevis halves 60, 62 together with the end effectors 58, 59 between them. As the clevis 56 and the end effectors 58, 59 are assembled as described, the bumps 67 on the inside surface of the clevis are deformed between coil loops by the radial inward pressing of them against the coil. This deformation prevents the coil from being pulled out of the clevis. Of course, if desired, other means such as welding, cementing, etc., can also be utilized to hold the coil in the clevis. In fact, where the endoscopic apparatus utilizes a laparoscopic type tube instead of a coil "tube" a different mechanism for holding the tube in the clevis is typically required.

Operation of the end effector assembly is best understood with reference to FIGS. 15 and 16. When the end effectors 58, 59 are in the open position as shown in FIG. 15, the push rod 16 is in the distal position. Squeezing the lever 24 of the actuator handle 18 (FIG. 1), moves the push rod 16 in the proximal direction. The distal hook 116 on the push rod 16 pulls the tangs 100 of the end effectors 58, 59 by virtue of its attachment through the holes 102 in the tangs 100. As the hook 116 moves proximally in the slots 86, the curved surface 106 on the tangs 100 engages the curved surfaces 76 of the sidewalls 72 of the grooves 70 in the respective clevis halves 60, 62. The engagement of these surfaces causes the end effectors to close to the position shown in FIG. 16. It will appreciated that the curvature of the surfaces 76, 106 will not only determine the rate at which the end effectors close, i.e., how much movement of the push rod 16 is needed to move the end effectors from the open to the closed position, but the rate of change in the rate at which the end effectors close. For example, by properly arranging the curvatures of the surfaces 76, 106, the end effectors can be arranged with constant linear movement of the push rod to accelerate, decelerate, or vary speeds in their closing motion.

When the end effectors 58, 59 are in the closed position as shown in FIG. 16, they are opened by moving the thumb ring 46 away from the finger ring 26 on the handle 18 (FIG. 1) which moves the push rod 16 in the distal direction. As the push rod 16 is moved in the distal direction, the distal hook 116 moves in the slots 86 and pushes the tangs 110 of the end effectors 58, 59 by virtue of its attachment to the holes 102 in the tangs 100. As the tangs 100 are pushed in the distal direction, the curved surfaces 104 on the tangs 100 engage the surfaces 78 on the sidewalls 74 of the grooves 70 in the respective clevis halves 60, 62. The engagement of these surfaces causes the end effectors 58, 59 to open to the position shown in FIG. 15. It will be appreciated again that the curvature of the surfaces 78, 104 will determine not only the rate at which the end effectors open, but the acceleration or deceleration, or speed change in the opening of the end effectors.

From the foregoing, those skilled in the art will appreciate that the curvature of the surfaces of the tangs of the end effectors and of the internal clevis grooves (76, 78, 104, and 106) may be chosen to provide for different rates and change of rates of opening and closing of the end effectors or they may be chosen to provide that the end effectors open and close at the same rates. It will also be appreciated that the rates and change of rates of opening and closing may be chosen to accommodate different types of end effectors. For example, it may be desirable for biopsy forceps to close quickly when taking a sample and open slowly so that the sample is not easily lost. In addition, in the quick closing of the biopsy forceps, in order to provide additional force it may be desirable for the end effectors to accelerate as they approach the closed position.

FIGS. 18 through 20 show a second embodiment of a clevis 156. The second embodiment of the clevis 156 is substantially the same as the embodiment described above with respect to the curved surfaces which interact with the tangs of the end effectors. However, the clevis 156 is different from the clevis 56 in the way that it attaches to the distal end of the coil 12. The clevis 156 is shorter than the clevis 56 and has a relatively small diameter proximal part 192 which has substantially the same outer diameter as the outer diameter of the coil 12. A stainless steel tube 164 is used to couple the clevis 156 to the coil 12 as shown in FIG. 18. The tube 154 fits over the distal end of the coil 12 and over the proximal part 192 of the clevis 156 and is coupled to both by either welding, crimping, gluing, or other suitable means. It will be appreciated that the distal portion 160 of the clevis has an outer diameter which is substantially the same as the outer diameter of the tube 164 after it is crimped. The tube 164 therefore forms a relatively smooth outer surface with the distal portion 160 of the clevis 156. In order to facilitate and/or enhance the coupling of the tube 164 with the coil 12, a distal portion 12a of the coil 12 may be ground slightly as shown in FIGS. 19 and 20 so that a greater surface area of the coil is presented to the tube 164 for attachment.

There has been described and illustrated an endoscopic forceps having a rack and pinion actuation handle and a track guided end effector assembly. While particular embodiments of the invention have been described, it is not intended that the invention be limited thereto, as it is intended that the invention be as broad in scope as the art will allow and that the specification be read likewise. Thus, while particular tube members and control members have been disclosed, it will be appreciated that other tube and control members could be utilized. Also, while two specific end effectors have been shown, it will be recognized that other types of end effectors could be used with similar results obtained. Moreover, while particular configurations have been disclosed in reference to the coupling of the coil and push rod to the actuator handle and to the clevis and end effectors, it will be appreciated that other configurations could be used as well. Furthermore, while the clevis has been disclosed as being made of two substantially identical plastic parts and held together with a sleeve, it will be understood that different materials and connecting means can achieve the same or similar function as disclosed herein, and the clevis halves need not be identical. In addition, while the invention was described substantially in terms of an endoscopic instrument with a coiled "tube" as is typical for a biopsy forceps device, it will be appreciated that the rack and pinion handle can be used with any type of endoscopic instrument, including instruments utilizing push rods, wires, laparoscopic type tubes, and different types of end effectors and end effector assemblies, including single acting instruments. Likewise, the end effector arrangement which opens and closes at desired rates and accelerations or decelerations, can be used in conjunction with other types of endoscopic instruments, including instruments having different types of handle arrangements, and instruments utilizing push rods, wires, laparoscopic type tubes, as well as single acting instruments, scissors, etc. The end effectors need not be identical and need not open and close at the same rates or with the same force. It will therefore be appreciated by those skilled in the art that yet other modifications could be made to the provided invention without deviating from its spirit and scope as so claimed.

We claim:

1. An actuator mechanism for use with an endoscopic instrument having a tube member, a control member extending through the tube member, and an end effector assembly coupled to the distal ends of the tube member and the control member whereby reciprocal movement of the control member through the tube member operates the end effector assembly, said actuator mechanism comprising:

a) a handle having a throughbore, with a proximal portion of said throughbore having a radial opening, and a distal portion of said throughbore for receiving the tube member to said handle;

b) a movable lever pivotally coupled to said handle, said lever having an upper toothed portion entering said proximal portion of said throughbore through said radial opening;

c) a rack member slidably disposed in said proximal portion of said throughbore and being engaged by said upper toothed part of said lever such that pivoting said lever relative to said handle moves said rack member along a longitudinal axis of said throughbore;

d) first coupling means for coupling said handle to the tube member; and e) second coupling means for coupling said rack member to the control member.

2. An actuator mechanism according to claim 1, wherein:

said throughbore is stepped, and said proximal portion of said throughbore has a relative larger diameter, and said distal portion of said throughbore has a relatively smaller diameter.

3. An actuator mechanism for use with an endoscopic instrument having a tube member, a control member extending through the tube member, and an end effector assembly coupled to the distal ends of the tube member and the control member whereby reciprocal movement of the control member through the tube member operates the end effector assembly, said actuator mechanism comprising:

a) a handle having a throughbore, with a proximal portion of said throughbore having a radial opening, and a distal portion of said throughbore for receiving the tube member to said handle;

b) a movable lever pivotally coupled to said handle, said lever having an upper toothed portion entering said proximal portion of said throughbore through said radial opening;

c) a rack member slidably disposed in said proximal portion of said throughbore and being engaged by said upper toothed part of said lever such that pivoting said lever relative to said handle moves said rack member along a longitudinal axis of said throughbore; and d) first coupling means for coupling said handle to the tube member, wherein,
said handle is stationary and is provided with a finger ring, and said lever is provided with a thumb ring.

4. An actuator mechanism according to claim 1, wherein:

said first coupling means comprises a radial bore extending from said distal part of said throughbore out of said stationary handle, and a first engagement member extending through said radial bore into said proximal part of said throughbore.

5. An actuator mechanism according to claim 4, wherein:

said radial bore is a radial slot in said stationary handle, and said engagement member is a U-shaped member.

6. An actuator mechanism according to claim 5, wherein: the tube member is a coil having turns, and said U-shaped member is a staple which engages the coil between the coil turns.

7. An actuator mechanism according to claim 1, wherein:

said second coupling means comprises a longitudinal bore in a distal end of said rack member, a radial bore intersecting said longitudinal bore, and an engagement member extending through said radial bore into said longitudinal bore.

8. An actuator mechanism according to claim 7, wherein: said engagement member is a set screw.

9. An actuator mechanism according to claim 1, wherein:

said rack member has a proximal electrical connector which extends out of a proximal end of said throughbore.

10. An actuator mechanism according to claim 1, wherein:

said first coupling means includes ferrule means fixedly coupled to said tube member and rotationally coupled to said handle, said ferrule means for rotating said tube member relative to said handle.

11. An actuator mechanism according to claim 10, wherein:

said ferrule means extends over a proximal portion of said handle.

12. An actuator mechanism according to claim 10, wherein:

said handle has receiving means for receiving said ferrule such that said ferrule is rotationally coupled to said handle.

13. An actuator mechanism according to claim 10, wherein:

said proximal portion of said throughbore is substantially cylindrical, and said rack member includes a shaft and a plurality of rounded cogs separated by grooves, and said upper tooth portion has a plurality of teeth engaging said grooves, wherein said rounded cogs rotate between said plurality of teeth in said substantially cylindrical throughbore.

14. An endoscopic instrument, comprising:

a) a tube member having a proximal end and a distal end;

b) a control member having a proximal end and a distal end and extending through said tube member;

c) an end effector assembly coupled to said distal end of said tube member and to said distal end of said control member; and d) an actuator mechanism having a handle, a movable lever, a rack member, first coupling means for coupling said handle to said tube member and second coupling means for coupling said rack to said control member, said handle having a throughbore, with a proximal portion of said throughbore having a radial opening, and a distal portion of said throughbore being coupled to said tube member by said first coupling means, said movable lever pivotally coupled to said handle, said lever having an upper toothed portion entering said proximal portion of said throughbore through said radial opening, and said rack member slidably disposed in said proximal portion of said throughbore and being engaged by said upper toothed part of said lever such that pivoting said lever relative to said handle moves said rack member along a longitudinal axis of said throughbore, said rack member being coupled to said control member by said second coupling means such that movement of said movable lever relative to said handle causes reciprocal movement of said control member through said tube member which operates said end effector assembly.

15. An endoscopic instrument according to claim 14, wherein:

said throughbore is stepped, and said proximal portion of said throughbore has a relative larger diameter, and said distal portion of said throughbore has a relatively smaller diameter.

16. An endoscopic instrument according to claim 15, wherein:

said second coupling means comprises a longitudinal bore in a distal end of said rack member, a radial bore intersecting said longitudinal bore, and an engagement member extending through said radial bore into said longitudinal bore.

17. An endoscopic instrument according to claim 15, wherein:

said first coupling means includes ferrule means fixedly coupled to said tube member and rotationally coupled to said handle, said ferrule means for rotating said tube member relative to said handle, said handle having receiving means for receiving said ferrule such that said ferrule is rotationally coupled to said handle.

18. An endoscopic instrument according to claim 10, wherein:

said proximal portion of said throughbore is substantially cylindrical, and said rack member includes a shaft and a plurality of rounded cogs separated by grooves, and said upper tooth portion has a plurality of teeth engaging said grooves, wherein said rounded cogs rotate between said plurality of teeth in said substantially cylindrical throughbore.

* * * * *